United States Patent
Morphy

(10) Patent No.: US 9,598,431 B1
(45) Date of Patent: Mar. 21, 2017

(54) COMPOUNDS USEFUL FOR INHIBITING ROR-GAMMA-T

(71) Applicant: Eli Lilly and Company, Indianapolis, IN (US)

(72) Inventor: John Richard Morphy, Guildford (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/256,892

(22) Filed: Sep. 6, 2016

Related U.S. Application Data

(60) Provisional application No. 62/215,929, filed on Sep. 9, 2015.

(51) Int. Cl.
  *C07D 495/20* (2006.01)
  *A61K 31/506* (2006.01)

(52) U.S. Cl.
  CPC .......... *C07D 495/20* (2013.01); *A61K 31/506* (2013.01)

(58) Field of Classification Search
  CPC ... A01B 12/006; C07D 495/20; A61K 31/506
  USPC .................... 514/278, 210; 544/70
  See application file for complete search history.

(56) References Cited

U.S. PATENT DOCUMENTS

| | | | | |
|---|---|---|---|---|
| 8,232,289 | B2 * | 7/2012 | Benito Collado ... | C07D 495/20 514/279 |
| 9,371,335 | B2 * | 6/2016 | Kehn .................. | A61K 31/435 |
| 2011/0118251 | A1 * | 5/2011 | Benito Collado ... | C07D 495/20 514/230.8 |
| 2012/0214784 | A1 * | 8/2012 | Benito Collado ... | C07D 495/20 514/210.2 |
| 2014/0309251 | A1 * | 10/2014 | Kehn .................. | A61K 31/435 514/278 |

FOREIGN PATENT DOCUMENTS

| WO | 2005/016913 | * | 2/2005 |
| WO | 2005/068183 | * | 7/2005 |

\* cited by examiner

*Primary Examiner* — Sabiha N Qazi
(74) *Attorney, Agent, or Firm* — Elizabeth A. Dingess-Hammond

(57) ABSTRACT

The present invention provides novel ROR gamma-t inhibitors and pharmaceutical compositions thereof:

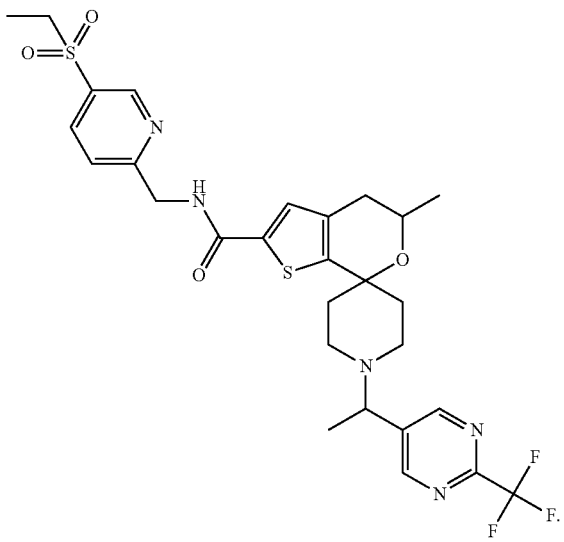

8 Claims, No Drawings

COMPOUNDS USEFUL FOR INHIBITING ROR-GAMMA-T

The present invention relates to compounds useful for inhibiting retinoic acid receptor-related orphan receptor gamma-t (RORγt), pharmaceutical compositions, and methods for treating diseases related to RORγ activity.

The retinoic acid receptor-related orphan receptors (RORs) are members of the nuclear receptor (NR) superfamily identified as important pathological regulators in many diseases. The ROR subfamily consists of RORα, RORβ, and RORγ. The mouse and human RORγ gene generates two isoforms, γ1 and γ2, the latter most commonly referred to as γt. RORγt signaling, often in response to IL-23/IL-23 receptor signaling, is required for the differentiation of naive CD4+ T-cells into a subset of T-cells designated Th17, which are distinct from the classical Th1 and Th2 cells, and supports their maintenance. Th17 cells produce interleukin-17A (IL-17) and IL-17F. In addition, Th17 cells produce a range of other factors known to drive inflammatory responses, including tumor necrosis factor-alpha (TNF-α), interleukin-6 (IL-6), GM-CSF, CXCL1 and CCL20. NK cells and innate lymphoid cells such as lymphoid tissue inducer (LTi)-like cells express IL-23 receptor and RORγt and produce IL-17 in response to stimulation and IL-23. There is substantial evidence that IL-23-responsive, RORγt, and IL-17-expressing cells are associated with autoimmune diseases (AI), inflammatory diseases, and cancer. Thus, targeted inhibition of RORγt may be important to reducing the pathogenesis of those diseases.

AI diseases are chronic conditions for which no cure currently exists. Treatment of AI diseases typically involves an attempt to control the process of the disease and decrease the symptoms by administering anti-inflammatory, anti-pain, or immunosuppressant medications. Unfortunately, the use of anti-inflammatory and anti-pain medications is sometimes ineffective and the use of immunosuppressants often leads to devastating long-term side effects. The most significant side effects of immunosuppressant drugs are an increased risk of infection and a higher risk of cancer.

Natural and synthetic ligands to RORγt have been identified. Small molecule inhibitors against RORγt have been reported in the literature for AI. See WO 2015/017335 and WO 2014/179564. However, the prevalence of AI diseases coupled with the ineffectiveness or devastating side effects of current treatments necessitate that more treatment choices be available to patients. Targeting RORγt may present an advantage over current AI therapies by maximizing the therapeutic benefit by targeting pathogenic immune cells while minimizing the risk of suppression of host defenses.

The present invention provides novel compounds that are RORγt inhibitors. Such new compounds could address the need for potent, effective treatment of uveitis, multiple sclerosis, rheumatoid arthritis, graft versus host disease, Crohn's disease, other inflammatory bowel diseases, cancer, psoriasis, and seronegative spondylarthropathies, such as axial spondyloarthritis, ankylosing spondylitis, and psoriatic arthritis.

The present invention provides a compound of formula

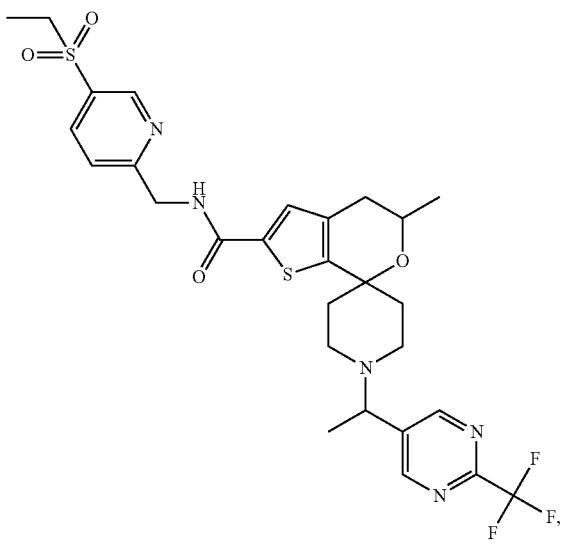 [SMILES: CCS(=O)(=O)c1ccc(CNC(=O)c2cc3c(s2)C2(CCN(C(C)c4cnc(C(F)(F)F)nc4)CC2)OC(C)C3)nc1]

or a pharmaceutically acceptable salt thereof.

The present invention also provides a method for the treatment of psoriasis in a patient comprising administering to a patient in need thereof a compound of the present invention, or a pharmaceutically acceptable salt thereof. Further, the present invention provides a method for the treatment of seronegative spondylarthropathies in a patient comprising administering to a patient in need thereof a compound of the present invention, or a pharmaceutically acceptable salt thereof. In said embodiment, seronegative spondylarthropathies are axial spondyloarthritis, ankylosing spondylitis, or psoriatic arthritis.

The present invention provides a pharmaceutical composition comprising a compound of the invention, or a pharmaceutically acceptable salt thereof, in combination with one or more pharmaceutically acceptable carriers, diluents, or excipients. In a further embodiment, the composition further comprises one or more other therapeutic agents. In a further embodiment, the present invention provides a pharmaceutical composition for the treatment of psoriasis comprising a compound of the invention, or a pharmaceutically acceptable salt thereof, in combination with one or more pharmaceutically acceptable carriers, diluents, or excipients. In yet a further embodiment, the present invention provides a pharmaceutical composition for the treatment of seronegative spondylarthropathies comprising a compound of the invention, or a pharmaceutically acceptable salt thereof, in combination with one or more pharmaceutically acceptable carriers, diluents, or excipients. In said embodiment, seronegative spondylarthropathies are axial spondyloarthritis, ankylosing spondylitis, or psoriatic arthritis.

Further, the present invention provides a compound of the invention, or a pharmaceutically acceptable salt thereof, for use in therapy, in particular for the treatment of psoriasis. Even further, the present invention provides a compound of the invention, or a pharmaceutically acceptable salt thereof, for use in the treatment of psoriasis. In a further embodiment, the present invention provides the use of a compound of the invention, or a pharmaceutically acceptable salt thereof, for the manufacture of a medicament for the treatment of psoriasis.

Further, the present invention provides a compound of the invention, or a pharmaceutically acceptable salt thereof, for use in therapy, in particular for the treatment of seronegative spondylarthropathies. Even further, the present invention provides a compound of the invention, or a pharmaceutically acceptable salt thereof, for use in the treatment of seronegative spondylarthropathies. In a further embodiment, the present invention provides the use of a compound of the invention, or a pharmaceutically acceptable salt thereof, for the manufacture of a medicament for the treatment of seronegative spondylarthropathies. In said embodiments, seronegative spondylarthropathies are of axial spondyloarthritis, ankylosing spondylitis, or psoriatic arthritis.

The present invention also encompasses intermediates and processes useful for the synthesis of a compound of the present invention.

The term "treating" (or "treat" or "treatment") as used herein refers to restraining, slowing, stopping, or reversing the progression or severity of an existing symptom, condition or disorder.

The term "spondylarthropathies" refers to a number of chronic joint diseases that generally involve the vertebral column and the areas where ligaments and tendons attach to bone. Spondylarthropathies are sometimes also called spondyloarthropathies or spondylo arthritis.

The term "seronegative" refers to a disease which is negative for reheumatoid factor.

A compound of the present invention may react to form pharmaceutically acceptable salts. Pharmaceutically acceptable salts and common methodology for preparing them are well known in the art. See, e.g., P. Stahl, et al. *Handbook of Pharmaceutical Salts: Properties, Selection and Use*, 2nd Revised Edition (Wiley-VCH, 2011); S. M. Berge, et al., "Pharmaceutical Salts," *Journal of Pharmaceutical Sciences*, Vol. 66, No. 1, Jan. 1977.

The skilled artisan will appreciate that a compound of the invention, as shown in (I), or pharmaceutically acceptable salt thereof, is comprised of a core that contains at least two chiral centers, as represented by * below:

(I)

Although the present invention contemplates all individual enantiomers, as well as mixtures of the enantiomers of said compounds including racemates, the preferred compounds of the invention are represented by (II) below:

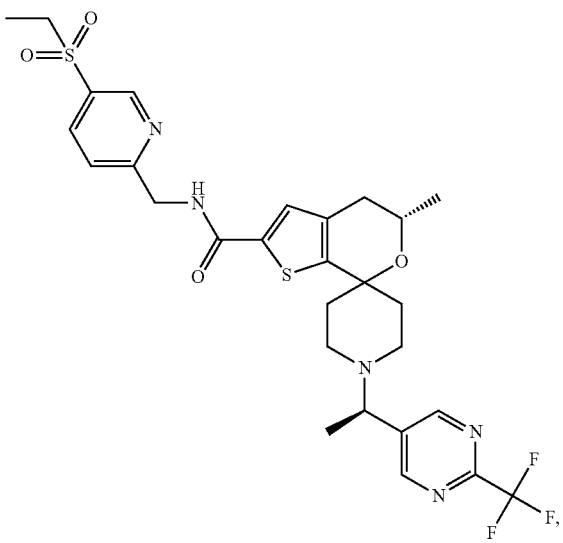 [SMILES: CCS(=O)(=O)c1ccc(CNC(=O)c2cc3c(s2)C2(CCN([C@H](C)c4cnc(C(F)(F)F)nc4)CC2)O[C@@H](C)C3)nc1]

(II)

or pharmaceutically acceptable salts thereof.

The skilled artisan will also appreciate that the Cahn-Ingold-Prelog (R) or (S) designations for all chiral centers will vary depending upon the substitution patterns of the particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. Single enantiomers of compounds of the invention are a preferred embodiment of the invention.

A compound of the present invention is preferably formulated as pharmaceutical compositions administered by a variety of routes. Such pharmaceutical compositions and processes for preparing the same are well known in the art. See, e.g., *Remington: The Science and Practice of Pharmacy* (A. Gennaro, et al., eds., 21st ed., Mack Publishing Co., 2005). More particularly preferred, is a pharmaceutical composition comprising a compound of the formula,

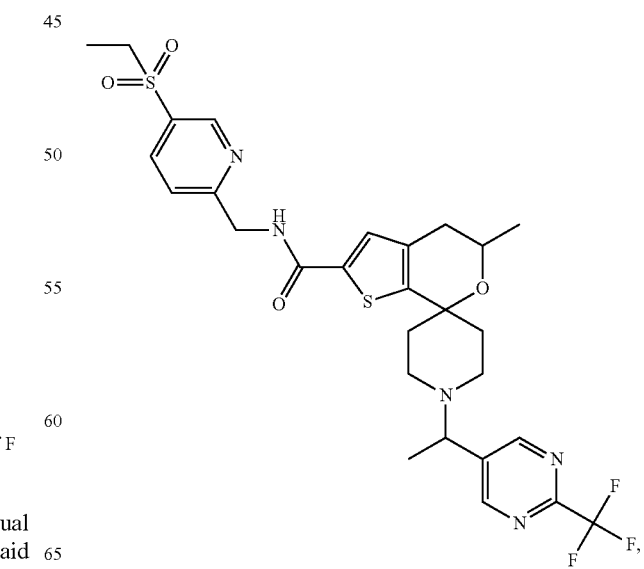

or a pharmaceutically acceptable salt thereof and one or more pharmaceutically acceptable carriers or diluents.

An especially preferred embodiment of the present invention relates to the compound, (5'S)—N-{[5-(ethylsulfonyl)pyridin-2-yl]methyl}-5'-methyl-1-{(1R)-1-[2-trifluoromethyl)pyrimidin-5-yl]ethyl}-4',5'-dihydrospiro[piperidine-4,7'-thieno[2,3-c]pyran]-2'-carboxamide:

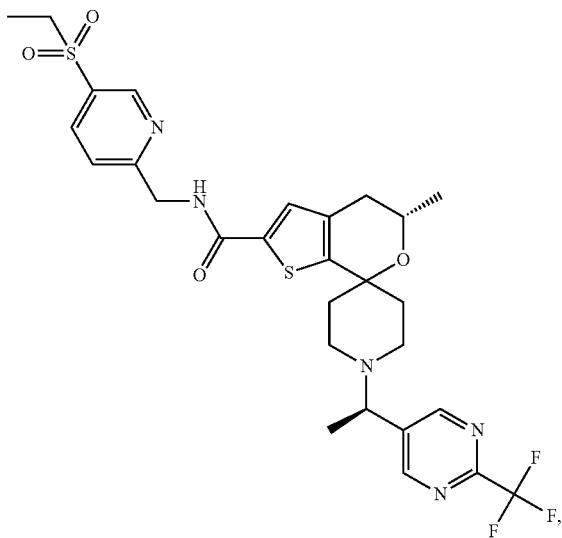

or a pharmaceutically acceptable salt thereof.

Another especially preferred embodiment of the present invention relates to the compound,

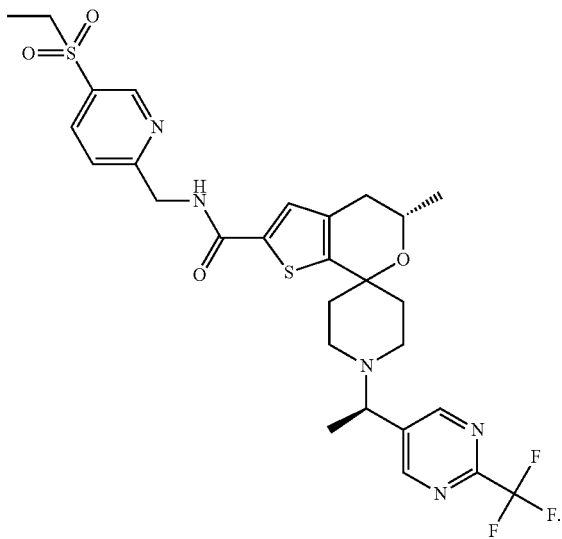 [SMILES: CCS(=O)(=O)c1ccc(CNC(=O)c2cc3c(s2)C2(CCN([C@H](C)c4cnc(C(F)(F)F)nc4)CC2)O[C@@H](C)C3)nc1]

The compounds of the present invention are generally effective over a wide dosage range. For example, dosages per day fall within the range of about 1 mg to 1 g. In some instances dosage levels below the lower limit of the aforesaid range may be more than adequate, while in other cases still larger doses may be employed while maintaining a favorable benefit/risk profile, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

Individual isomers, enantiomers, and diastereomers may be separated or resolved by one of ordinary skill in the art at any convenient point in the synthesis of compounds of Formula I, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). The designations "isomer 1" and "isomer 2" refer to the compounds that elute from chiral chromatography first and second, respectively, and if chiral chromatography is initiated early in the synthesis, the same designation is applied to subsequent intermediates and examples.

Additionally, certain intermediates described herein may contain one or more protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Certain abbreviations are defined as follows: "AUC" refers to area under the curve; "BSA" refers to Bovine Serum Albumin; "CFA" refers to complete Freund's adjuvant; "DBA" refers to dilute brown non-Agouti; ""DCM" refers to dichloromethane; DPBS" refers to Dulbecco's phosphate-buffered saline; "DMEM" refers to Dulbecco's Modified Eagle's Medium; "DMSO" refers to dimethyl sulfoxide; "$EC_{50}$" refers to the effective concentration at half the maximal response; "EtOAc" refers to ethyl acetate; "$Et_2O$" refers to ethyl ether; "EtOH" refers to ethyl alcohol or ethanol; "ee" refers to enantiomeric excess; "Ex" refers to example; "FBS" refers to Fetal Bovine Serum; "G" refers to gravitational force; "GAL" refers to beta-galactosidase DNA binding domain; "GPI" refers to glucose -6-phosphate isomerase; "HEC" refers to hydroxy ethyl cellulose; "HEK" refers to human embryonic kidney; "HEPES" refers to 4-(2-hydroxyethyl)-1-piperazineethanesulfonic acid; "$IC_{50}$" refers to the concentration of an agent that produces 50% of the maximal inhibitory response possible for that agent; "IL" refers to interleukin; "IPA" refers to isopropyl alcohol or isopropanol; "Kd" refers to constant of dissociation; "Ki" refers to inhibition constant; "MeOH" refers to methyl alcohol or methanol; "MEM" refers to Minimum Essential Medium; "PBMC" refers to peripheral blood mononuclear cells; "PBS" refers to phosphate buffered saline; "Prep" refers to preparation; "RAR refers to retinoic acid receptor; and "RPMI" refers to Roswell Park Memorial Institute. "$R_t$" refers to retention time; "SCX" refers to strong cation exchange; "SFC" refers to supercritical fluid chromatography; and "THF" refers to tetrahydrofuran.

The compounds of the present invention, or salts thereof, may be prepared by a variety of procedures known in the art, some of which are illustrated in the Preparations and Examples below. The specific synthetic steps for each of the routes described may be combined in different ways to prepare compounds of the invention, or salts thereof. The products of each step below can be recovered by conventional methods well known in the art, including extraction, evaporation, precipitation, chromatography, filtration, trituration, and crystallization. The reagents and starting materials are readily available to one of ordinary skill in the art.

The following preparations and examples further illustrate the invention and represent typical synthesis of the compounds of the present invention.

PREPARATIONS AND EXAMPLES

Preparation 1

1-(3-Thienyl)propan-2-one

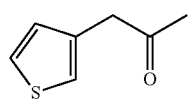

Suspend 2-(3-thienyl)acetic acid (26.5 g, 146.5 mmol) in acetic anhydride (87.9 mL, 913 mmol,) and add 1-methylimidazole (7.57 g, 91.3 mmol). Stir the reaction mixture for 4 hours at room temperature under nitrogen. Cool the reaction mixture to 0° C., add water (150 mL), and stir for 1 hour. Dilute the solution with EtOAc (300 mL) and wash successively with 2 M NaOH (2×200 ml), water (200 mL) and brine (200 mL). Separate the organic extracts phase, dry over sodium sulfate, filter, and concentrate to dryness to obtain the title compound (28.16 g, 77%) as a yellow oil. $^1$H NMR (400.13 MHz, CDCl$_3$) δ 2.14 (s 3H), 3.7 (s, 2H), 6.94 (d, J=5.1 Hz, 1H), 7.08 (bs, 1H), 7.29-7.26 (m, 1H).

Preparation 2

1-(3-Thienyl)propan-2-ol

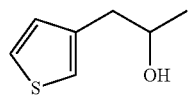

Add dry MeOH (63 mL) to sodium borohydride (1.61 g, 41.67 mmol) and cool the reaction mixture to −10° C. while adding the MeOH. Cool further to −20° C. and add a solution of 1-(3-thienyl)propan-2-one (4.92 g, 33.34 mmol) in dry MeOH (26.7 mL) dropwise over 40 minutes and stir for 1.5 hours at −20° C. then at room temperature for 17 hours. Cool the solution to −5° C. (internal temperature) and quench with a saturated solution of ammonium chloride (15 ml) then with 1 N HCl (15 mL). Add water (30 mL) and EtOAc (100 mL). Concentrate the mixture under reduced pressure to ⅓ of total volume. Extract the mixture with EtOAc (2×100 mL). Combine the organic extracts and dry over magnesium sulfate, filter, and concentrate to dryness to give the title compound (4.74 g, 100%). Mass spectrum (m/z): 125 (M−OH+H), 164.8 (M+Na).

Alternate Preparation 2a

Add sodium borohydride (7.06 g, 182.8 mmol) portion wise over 30 minutes at 0° C. to a solution of 1-(3-thienyl)propan-2-one (28.16 g, 140.6 mmol) in MeOH (282 mL) and stir at room temperature overnight. Concentrate to dryness, dilute with EtOAc (200 mL) and wash with a saturated solution of ammonium chloride (150 mL). Extract the aqueous layer with EtOAc (2×200 mL). Combine the organic extracts, dry over sodium sulfate, filter, and concentrate under reduced pressure. Purify the residue by silica gel flash chromatography eluting with MeOH: DCM (0:100 to 5:95) to give the title compound (12.85 g, 64%) as a pale red oil. Mass spectrum (m/z): 125 (M−OH+H).

Preparation 3

(2S)-1-(3-Thienyl)propan-2-ol

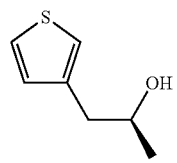

Dissolve 3-bromothiophene (6.88 g, 42.2 mmol) in anhydrous THF (10 mL) and toluene (100 mL). Cool to −78° C. To this add via syringe sec-butyllithium (1.3 mol/L in cyclohexane, 34 mL, 44 mmol) over 15 minutes. Maintain the temperature at <−60° C., stir 10 minutes, then add (2S)-2-methyloxirane (4.9 g, 84.4 mmol) dropwise. After 5 minutes, add boron trifluoride diethyl etherate (5.3 mL, 42 mmol) over 15 minutes via dropping funnel. Maintain the temperature at <−55° C. After the addition is complete, stir at −78° C. for 2 hours. Quench at −78° C. with saturated sodium bicarbonate, add Et$_2$O, and warm to ambient temperature. Wash with saturated sodium bicarbonate (2×) followed by saturated brine. Dry the organic layer over sodium sulfate, filter, and concentrate under reduced pressure. Purify by silica gel flash chromatography eluting with 15% EtOAc/hexanes to give the title compound (3.85 g, 64.2%). Repurify the mixed fractions to give a total amount of the title compound (4.29 g, 71.5%) as a colorless liquid. $^1$H NMR (400.13 MHz, CDCl$_3$) δ 7.28-7.26 (dd, J=2.9, 5.0, 1H), 7.03-7.01 (m, 1H), 6.96 (dd, J=1.2, 4.9, 1H), 4.04-3.95 (m, 1H), 2.83-2.68 (m, 2H), 1.63 (s, 1H), 1.22 (d, J=6.2, 3H), OR [α]$^{20}$D+25.50 (c 1.00, CHCl$_3$), Preparation 4

(5'S)-5-Methyl-4',5'-dihydrospiro[piperidine-4,7'-thieno[2,3-c]pyran]

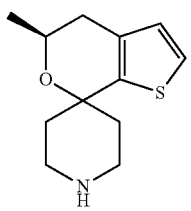

Dissolve tert-butyl 4-oxopiperidine-1-carboxylate (6.50 g, 32.6 mmol) and (2S)-1-(3-thienyl)propan-2-ol (4.64 g, 32.6 mmol) in DCM (100 mL). Add trifluoroacetic acid (20 mL, 264.5 mmol). Stir the mixture at ambient temperature 18 hours. Concentrate the mixture under reduced pressure, and then add water and Et$_2$O. Wash the organic layer with water, combine the aqueous washes, and then adjust pH to basic with solid sodium carbonate. Saturate the aqueous layer with solid sodium chloride, then wash aqueous layer with EtOAc (5×). Combine the EtOAc layers, wash with brine, dry with sodium sulfate, filter, and concentrate under reduced pressure to give the title compound (4.61 g, 63%) as a pale yellow oil. Mass spectrum (m/z): 224.2 (M+H).

Preparation 5 tert-Butyl (5'S)-5'-methyl-4',5'-dihydro-1H-spiro[piperidine-4,7'-thieno[2,3-c]pyran]-1-carboxylate

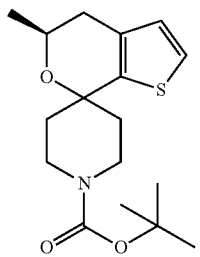 [SMILES: C[C@H]1Cc2ccsc2C2(CCN(C(=O)OC(C)(C)C)CC2)O1]

Dissolve (5'S)-5'-methyl-4',5'-dihydrospiro[piperidine-4,7'-thieno[2,3-c]pyran] (10.39 g, 46.53 mmol) in DCM (100 mL). Add di-tert-butyl dicarbonate (11.52 mL, 51.18 mmol) dropwise and stir the mixture at ambient temperature for 1.5 hours. Add additional di-tert-butyl dicarbonate (2.00 mL, 9.17 mmol) and stir 30 minutes, then concentrate under reduced pressure. Add imidazole (2.21 g, 32.5 mmol) to destroy excess di-tert-butyl dicarbonate (Synthesis, 2001, No. 4, 550). Add Et$_2$O and wash with brine. Dry the organic layer over sodium sulfate, filter, and concentrate under reduced pressure. Purify by silica gel flash chromatography eluting with 10% EtOAc/hexanes. Re-purify by silica gel flash chromatography eluting with 15% EtOAc/hexanes to give the title compound (12.92 g, 86%) as a colorless oil. $^1$H NMR (400.13 MHz, d$_6$-DMSO) δ 7.33 (d, J=5.1, 1H), 6.77 (d, J=5.1, 1H), 3.92-3.72 (m, 3H), 3.15-2.91 (s, 2H), 2.62 (dd, J=15.8, 3.0, 1H), 2.30 (dd, J=15.8, 10.6, 1H), 2.1 (m, 1H), 1.76-1.63 (m, 2H), 1.51-1.40 (m, 1H), 1.38 (s, 9H), 1.24 (d, J=6.2, 3H), 100% ee based on SFC chromatography, Lux Amylose-2, 5 mL/min, 225 nm, R$_t$=1.75 min, OR [α]$^{20}$D+82.1 (c 1.00, CHCl$_3$).

Preparation 6 tert-Butyl-5'-methyl-4',5'-dihydro-1H-spiro[piperidine-4,7'-thieno[2,3-c]pyran]-1-carboxylate

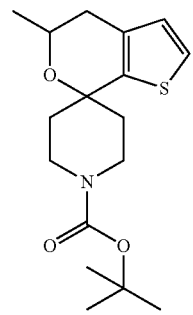 [SMILES: CC1Cc2ccsc2C2(CCN(C(=O)OC(C)(C)C)CC2)O1]

Add trifluoroacetic acid (34.16 mL, 451.8 mmol) dropwise at 0° C. to a solution of 1-(3-thienyl)propan-2-ol (12.85 g, 90.35 mmol) and tert-butyl 4-oxopiperidine-1-carboxylate (23.40 g, 117.5 mmol) in dry DCM (135 mL) and maintain stirring at room temperature for 17 hours. Concentrate the mixture to dryness, dilute the residue with MeOH, and then remove the solvent under reduced pressure. Take up the residue in MeOH and purify by ion exchange chromatography. Combine the layers containing the desired product and concentrate under reduced pressure co-evaporating with toluene (3×) to give a pale orange solid of crude 5-methylspiro[4,5-dihydrothieno[2,3-c]pyran-7,4'-piperidine]. Add 4-dimethylaminopyridine (2.23 g, 18.07 mmol) and triethylamine (37.8 mL, 271.1 mmol) dropwise to a solution of 5-methylspiro[4,5-dihydrothieno[2,3-c]pyran-7,4'-piperidine] (20.18 g, 90.35 mmol) in dry DCM (90.35 mL) cooled to 0° C. To this add dropwise a solution of di-tert-butyl dicarbonate (30.49 g, 135.5 mmol,) in dry DCM (27.1 mL). Stir at room temperature overnight. Add water (100 mL), extract the aqueous layer with DCM (3×100 mL), wash with brine (100 mL), and concentrate under reduced pressure. Purify by silica gel flash chromatography eluting with EtOAc: iso-hexane (0:100 to 20:80). Co-evaporate the residue with DCM (3×) to give the title compound (27.64 g, 92.7%) as a white solid. Mass spectrum (m/z): 346 (M+Na)

Alternate Preparation 6a tert-Butyl-5'-methyl-4',5'-dihydro-1H-spiro[piperidine-4,7'-thieno[2,3-c]pyran]-1-carboxylate Add trifluoroacetic acid (20.17 mL, 266.72 mmol) dropwise at 0° C. to a solution of 1-(3-thienyl)propan-2-ol (4.74 g, 33.34 mmol) and tert-butyl 4-oxopiperidine-1-carboxylate (7.80 g, 38.34 mmol) in dry DCM (100 mL) and stir at room temperature overnight. Concentrate the mixture to dryness and dilute the residue with MeOH. Purify the crude material by ion exchange chromatography. Combine the layers containing the desired product and concentrate under reduced pressure co-evaporating with DCM (3×) to give crude 5-methylspiro[4,5-dihydrothieno[2,3-c]pyran-7,4'-piperidine] (8.17 g). Add 4-dimethylaminopyridine (0.831 g, 6.67 mmol) and triethylamine (9.29 mL, 66.68 mmol) to a solution of 5-methylspiro[4,5-dihydrothieno[2,3-c]pyran-7,4'-piperidine] (8.17 g) in dry DCM (66.7 mL) cooled to 0° C. To this add dropwise a solution of di-tert-butyl dicarbonate (18.19 g, 83.35 mmol,) in dry DCM (16.7 mL). Stir at room temperature for 3 days. Add water (60 mL), extract the aqueous layer with DCM (3×50 mL), wash with brine (20 mL), filter through a phase separator, and concentrate under reduced pressure. Purify the residue by silica gel flash chromatography eluting with EtOAc: iso-hexane (0:100 to 20:80). Co-evaporate the residue with DCM (2×) to give the title compound (9.41 g, 80%). Mass spectrum (m/z): 346 (M+Na)

Preparation 7

1-(tert-Butoxycarbonyl)-5'-methyl-4',5'-dihydrospiro[piperidine-4,7'-thieno[2,3-c]pyran]-2'-carboxylic acid

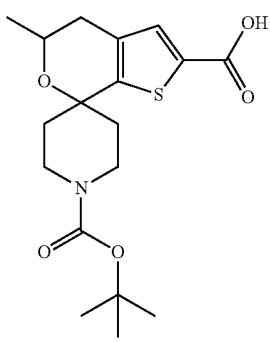 [SMILES: CC1Cc2cc(C(=O)O)sc2C2(CCN(C(=O)OC(C)(C)C)CC2)O1]

Dissolve tert-butyl-5'-methyl-4',5'-dihydro-1H-spiro[piperidine-4,7'-thieno [2,3-c]pyran]-1-carboxylate (7.16 g, 21.71 mmol) in THF (108.5 mL) and cool to −78° C. To this add butyllithium (2.5 M in hexanes, 13 mL, 32.56 mmol) dropwise over 20 minutes and stir the mixture an additional 30 minutes after addition is complete. Bubble in $CO_2$ via cannula and maintain stirring at this temperature for 1 hour with continuous addition of $CO_2$. Allow the reaction to warm to 0° C. over 2 hours with continuous addition of $CO_2$ and quench carefully with water (80 mL). Pour the reaction mixture into water and extract the aqueous layer with $Et_2O$ (100 mL). Wash the organic phase with 2 N NaOH (3×15 mL) and water (50 mL). Acidify the aqueous layer with 2 N HCl (3×) to pH=6, and extract with EtOAc. Combine the organic extracts and wash with brine (50 mL), dry over magnesium sulfate, filter, and concentrate under reduced pressure to obtain the title compound (7.89 g, 97%) as an off-white solid. Mass spectrum (m/z): 390 (M+Na).

Preparation 8

1-(tert-Butoxycarbonyl)-4',5'-dihydrospiro[piperidine-4,7'-thieno[2,3-c]pyran]-2'-carboxylic acid

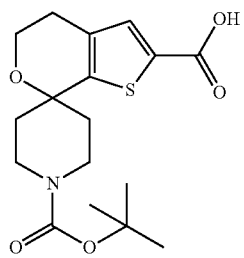 [SMILES: CC(C)(C)OC(=O)N1CCC2(CC1)OCCc1cc(C(=O)O)sc12]

Dissolve tert-butyl-4,5'-dihydro-1H-spiro[piperidine-4,7'-thieno[2,3-c]pyran]-1-carboxylate (prepared as described in J. Med. Chem., 2011, 54, (8), pp 2687-2700 and WO2011060035) (10 g, 32.32 mmol) in THF (100 mL) and cool to −78° C. To this add butyllithium (22.22 mL, 35.55 mmol) dropwise over 15 minutes and stir the mixture an additional 15 minutes after addition is complete. Bubble in $CO_2$ via cannula and allow the mixture to warm to room temperature with continuous addition of $CO_2$. After 2 hours, cool the mixture to 0° C., and add water followed by $Et_2O$. Basify the aqueous layer with 1 N NaOH and wash the organic layer with 1 N NaOH (3×). Combine the base washes and acidify to pH 2 with 5 N HCl. Wash the aqueous layer with EtOAc (3×), combine the organic extracts, and wash with brine. Dry over sodium sulfate, filter, and concentrate under reduced pressure to give the title compound (11.11 g, 97.27%) as a white solid. Mass spectrum (m/z): 352.2 (M−H).

Preparation 9

(5'S)-1-tert-Butoxycarbonyl)-5'-methyl-4',5'dihydrospiro[piperidine-4,7'-thieno[2,3-c]pyran]-2'-carboxylic acid

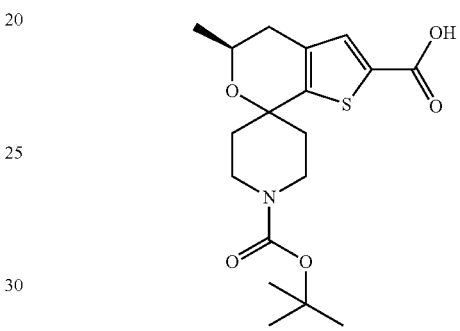

Dissolve tert-butyl (5'S)-5'-methyl-4',5'-dihydro-1H-spiro [piperidine-4,7'-thieno[2,3-c]pyran]-1-carboxylate (11.19 g, 34.60 mmol) in anhydrous THF (200 mL) and cool to −78° C. Add n-butyllithium (21 mL, 34.64 mmol) dropwise over 20 minutes. After addition is complete, stir at −78° C. for 20 minutes, then bubble in $CO_2$ gas via cannula for 60 minutes. Warm the mixture to room temperature with continuous addition of $CO_2$. After stirring 1 hour at room temperature, quench with water (3 mL) and concentrate under reduced pressure to 25% volume. Add $Et_2O$ and water. Wash with water (2×) and combine the aqueous washes. Adjust the pH to acidic with 1 N HCl. Saturate the aqueous layer with sodium chloride and extract with EtOAc (2×). Combine the EtOAc extracts, wash with brine, dry over sodium sulfate, filter, and concentrate under reduced pressure to give the title compound (13.40 g, 100%) as a white foam. Mass spectrum (m/z): 366 (M−H).

Preparation 10

5-(Ethylsulfanyl)pyridine-2-carbonitrile

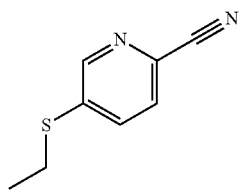

Dissolve 5-bromopyridine-2-carbonitrile (49.42 g, 270.1 mmol) and potassium carbonate (113.5 g, 821.2 mmol) in 1-methyl-2-pyrrolidinone (280 mL) and add ethanethiol (26.4 mL, 356 mmol) in portions over 30 minutes such that temperature stays below 50° C. Cool the reaction to room temperature and stir overnight. Dilute with EtOAc (1200 mL) and water (2200 mL). Collect the organic layer and wash with brine (3×300 mL), dry the organic layer over sodium sulfate, filter, and concentrate under reduced pressure to give the title compound (44.87 g, 100%) as an off white solid. $^1$H NMR (400.13 MHz, d$_6$-DMSO) δ 8.63 (s, 1H), 7.93 (s, 2H), 3.17 (q, J=7.3, 2H), 1.29 (t, J=7.3, 3H).

Preparation 11

5-(Ethylsulfonyl)pyridine-2-carbonitrile

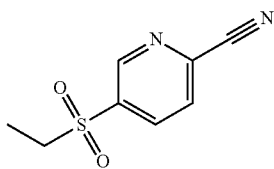

Dissolve 5-(ethylsulfanyl)pyridine-2-carbonitrile (44.36 g, 270.1 mmol) in anhydrous DCM (540 mL) and cool to −20° C. Add 3-chloroperoxybenzoic acid (130 g, 565.0 mmol) in 10-12 gram portions over 1 hour maintaining an internal temperature between 0° C. and −10° C. Stir the reaction mixture in a cold bath allowing to warm to room temperature overnight. Wash with 1 N NaOH (1 L), water, 1 N NaOH (2×500 mL), and brine. Dry the organic layer over sodium sulfate, filter, and concentrate under reduced pressure to give the title compound (49.52 g, 93%) as a white solid. $^1$H NMR (400.13 MHz, d$_6$-DMSO) δ 9.20 (d, J=1.9, 1H), 8.56 (dd, J=2.0, 8.1, 1H), 8.36 (d, J=8.1, 1H), 3.52 (q, J=7.3, 2H), 1.16 (t, J=7.5, 3H).

Preparation 12

1-[5-(Ethylsulfonyl)pyridine-2-yl]methanamine hydrochloride

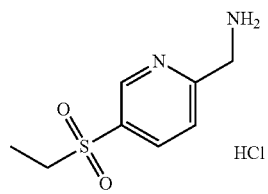

Divide 5-(ethylsulfonyl)pyridine-2-carbonitrile (49.52 g, 252.4 mmol) into three 16.5 g portions. Under N$_2$ in a 2250 mL Parr bottle, add 10% Pd/C (1.65 g, 15.5 mmol) to the vessel and wet with MeOH (750 mL). Add to this 5-(ethylsulfonyl)pyridine-2-carbonitrile (16.5 g, 84.09 mmol) dissolved in MeOH (750 mL). Add to this HCl (6N aqueous, 17.1 ml, 102.6 mmol). Seal the bottle, purge with N$_2$, purge with H$_2$, and pressurize to 68.9 kPa at room temperature for 3 hours. Purge with N$_2$, and then filter the mixture. Repeat on the remaining portions of 5-(ethylsulfonyl)pyridine-2-carbonitrile. Combine all filtrates and concentrate under reduced pressure to give the title compound (59.61 g, 99%) as a beige solid. Mass spectrum (m/z): 201 (M+H−HCl).

Preparation 13 tert-Butyl 2'-({[5-(ethylsulfonyl)pyridine-2-yl]methyl}carbamoyl)-5'-methyl-4',5'-dihydro-1H-spiro[piperidine-4,7'-thieno[2,3-c]pyran]-1-carboxylate

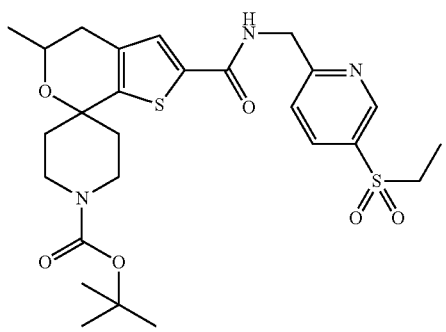 [SMILES: CCS(=O)(=O)c1ccc(CNC(=O)c2cc3c(s2)C2(CCN(C(=O)OC(C)(C)C)CC2)OC(C)C3)nc1]

Dissolve 1-[5-(ethylsulfonyl)pyridine-2-yl]methanamine hydrochloride (3.1 g, 13 mmol), 1-(tert-butoxycarbonyl)-5'-methyl-4',5'-dihydrospiro[piperidine-4,7'-thieno[2,3-c]pyran]-2'-carboxylic acid (3.9 g, 10 mmol) in anhydrous DCM (52 mL). Cool to 0° C. and add trimethylamine (10 mL, 73 mmol) dropwise followed by a 1.67 M solution of 2,4,6-tripropyl-1,3,4,2,4,6-trioxatriphosphorinane-2,4,6-trioxide (8.6 g, 14 mmol) in EtOAc. Allow the mixture to warm to room temperature and stir overnight. Carefully add water (50 mL) and stir 10 minutes at room temperature. Extract the aqueous layer with DCM (2×), then combine the organic extracts. Wash the organic extracts with brine, dry over sodium sulfate, filter, and concentrate under reduced pressure. Purify the crude material with silica gel chromatography eluting with a 50% to 100% EtOAc/hexanes gradient to give the title compound (4.89 g, 83%) as a yellow foam. Mass spectrum (m/z): 550 (M+H).

Preparation 14 tert-Butyl (5'S)-2'-({[5-(ethylsulfonyl)pyridine-2-yl]methyl}carbamoyl)-5'-methyl-4',5'-dihydro-1H-spiro[piperidine-4,7'-thieno[2,3-c]pyran]-1-carboxylate

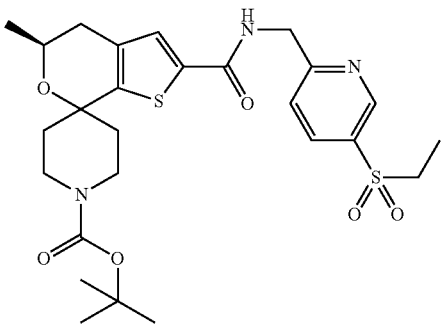 [SMILES: CCS(=O)(=O)c1ccc(CNC(=O)c2cc3c(s2)C2(CCN(C(=O)OC(C)(C)C)CC2)O[C@@H](C)C3)nc1]

Dissolve 1-[5-(ethylsulfonyl)pyridine-2-yl]methanamine hydrochloride (2.86 g, 10.5 mmol), (5'S)-1-tert-butoxycarbonyl)-5'-methyl-4',5'dihydrospiro[piperidine-4,7'-thieno[2,3-c]pyran]-2'-carboxylic acid (3.50 g, 9.52 mmol), and 1-hydroxybenzotriazole (1.44 g, 10.5 mmol) in anhydrous THF (100 mL) and dimethylformamide (50 mL). Add N,N- diisopropylethylamine (4.98 mL, 28.6 mmol) followed by 1-(3-dimethylaminopropy)-3-ethylcarbodiimide hydrochloride and allow to stir at room temperature overnight. Concentrate under reduced pressure to ~40% volume, then add EtOAc. Wash with saturated sodium bicarbonate (2×), water (2×), brine (2×), dry the organic layer over sodium sulfate, filter, and concentrate under reduced pressure. Chromatograph on silica gel with 80% EtOAc/hexanes to give the title compound (4.51 g, 86%) as a grey foam. Mass spectrum (m/z): 550 (M+H).

Preparation 15

N-{[5-(Ethyl sulfonyl)pyridine-2-yl]methyl}-5'-methyl-4',5',dihydrospiro[piperidine-4,7'-thieno[2,3,c]pyran]-2'-carboxamide dihydrochloride

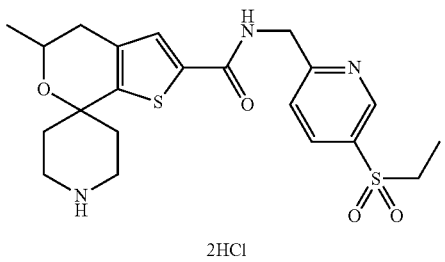 [SMILES: CCS(=O)(=O)c1ccc(CNC(=O)c2cc3c(s2)C2(CCNCC2)OC(C)C3)nc1]

2HCl

Dissolve tert-butyl 2'-({[5-(ethylsulfonyl)pyridine-2-yl]methyl}carbamoyl)-5'-methyl-4',5'-dihydro-1H-spiro[piperidine-4,7'-thieno[2,3,c]pyran]-1-carboxylate (0.95 g, 1.68 mmol) in MeOH (10 mL) and add 4 M HCl in dioxane (4.5 mL, 18 mmol). Stir at room temperature for 1 hour, then concentrate under reduced pressure to give the title compound (0.86 g, 100%) as a white solid. Mass spectrum (m/z): 450 (M+H−2HCl).

Preparation 16

(5'S)—N-{[5-(Ethylsulfonyl)pyridine-2-yl]methyl}-5'-methyl-4',5',dihydrospiro[piperidine-4,7'-thieno[2,3,c]pyran]-2'-carboxamide dihydrochloride

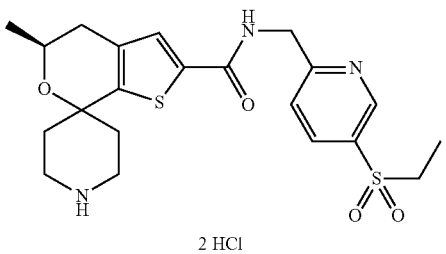 [SMILES: CCS(=O)(=O)c1ccc(CNC(=O)c2cc3c(s2)C2(CCNCC2)O[C@@H](C)C3)nc1]

2 HCl

Dissolve tert-butyl (5'S)-2'-({[5-(ethylsulfonyl)pyridine-2-yl]methyl}carbamoyl)-5'-methyl-4',5'-dihydro-1H-spiro[piperidine-4,7'-thieno[2,3,c]pyran]-1-carboxylate mmol (1.14 g, 2.0 mmol) in 1,4 dioxane (10 mL) and MeOH (5 mL). Add 4 M HCl in dioxane (5.0 mL, 20 mmol) and stir at room temperature for 2 hours. Concentrate to about 10 mL, then add Et₂O and stir vigorously overnight. Add hexanes, filter, and rinse with hexanes to give the title compound (0.99 g, 91%) as a light yellow solid. Mass spectrum (m/z): 450 (M+H−2HCl).

Preparation 17

1-[2-(Trifluoromethyl)pyrimidin-5-yl]ethanol

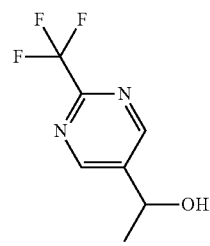

Dissolve 2-(trifluoromethyl)pyrimidine-5-carbaldehyde (11.31 mmol, 1.992 g) in THF (56.56 mL), cool to 0° C., and slowly add methylmagnesium bromide (3 M in Et₂O) (33.94 mmol, 11.31 mL). Allow the reaction to warm to room temperature and stir for 2.5 hours. Quench the reaction with 1 N HCl. Add EtOAc and wash with 1 N HCl. Dry the organics over sodium sulfate, filter, and concentrate under reduced pressure to give the title compound (1.663 g, 76.5%). Mass spectrum (m/z): 193.0 (M+H).

Preparation 18

5-(1-Bromoethyl)-2-(trifluoromethyl)pyrimidine

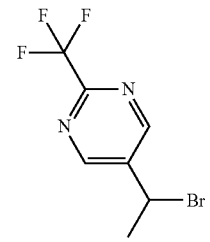

Dissolve 1-[2-(trifluoromethyl)pyrimidin-5-yl]ethanol (8.655 mmol, 1.663 g) and triphenylphosphine (12.98 mmol, 3.405 g) in DCM (86.55 mL) and add N-bromosuccinimide (12.98 mmol, 2.311 g) at room temperature. After three hours, concentrate the reaction under reduced pressure. Purify the resulting residue via silica gel chromatography eluting with 10% EtOAc/hexanes to give the title compound (1.641 g, 74.34%). ¹H NMR (400.13 MHz, d₆-DMSO) δ 9.26 (s, 2H), 5.63 (q, J=7.0 Hz, 1H), 2.09 (d, J=7.0 Hz, 3H).

EXAMPLE 1

N-{[5-(Ethylsulfonyl)pyridine-2-yl]methyl}-5'-methyl-1-{1-[2-(trifluoromethyl)pyrimidin-5-yl]ethyl}-4',5'-dihydrospiro[piperidine-4,7'thieno[2,3-C]pyran]-2'-carboxamide

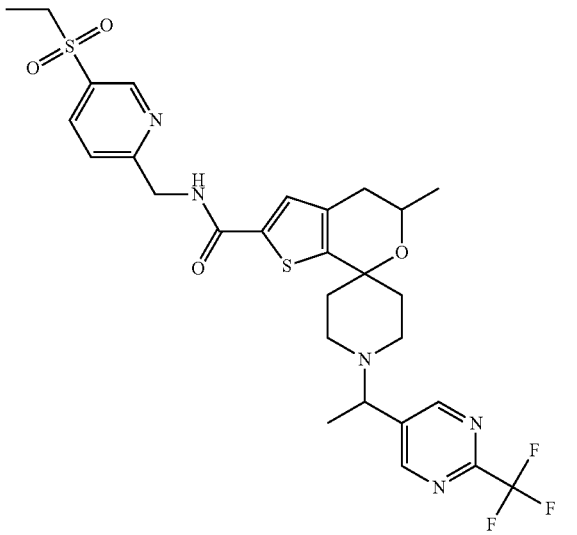 [SMILES: CCS(=O)(=O)c1ccc(CNC(=O)c2cc3c(s2)C2(CCN(C(C)c4cnc(C(F)(F)F)nc4)CC2)OC(C)C3)nc1]

Dissolve N-{[5-(ethylsulfonyl)pyridine-2-yl]methyl}-5'-methyl-4',5',dihydrospiro[piperidine-4,7'-thieno[2,3,c]pyran]-2'-carboxamide dihydrochloride (1.12 g, 2.31 mmol) in acetonitrile (11.6 mL) and diisopropylethylamine (2.42 mL, 13.9 mmol) and add 5-(1-bromoethyl)-2-(trifluoromethyl) pyrimidine (0.71 g, 2.77 mmol). Heat the mixture at 60° C. for 90 minutes, then cool to ambient temperature and concentrate under reduced pressure. Dissolve the crude mixture in MeOH (5 mL), then load onto a 50 g SCX column. Flush with MeOH (150 mL) and then elute product with 2 N ammonia/MeOH (150 mL). Concentrate the ammonia/MeOH washes under reduced pressure to an orange foam. Chromatograph the crude material with silica gel chromatography eluting with a 100% DCM to 95% DCM/MeOH gradient to give the title compound (1.54 g, 43%). Mass spectrum (m/z): 624 (M+H).

EXAMPLE 2

(5S')—N-{[5-(Ethylsulfonyl)pyridine-2-yl]methyl}-5'-methyl-1-{(1S)-1-[2-(trifluoromethyl)pyrimidin-5-yl]ethyl}-4',5'-dihydrospiro[piperidine-4,7'thieno[2,3-C]pyran]-2'-carboxamide

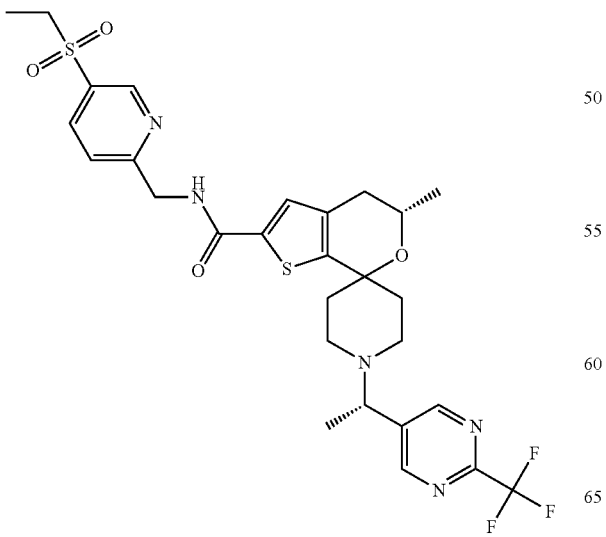

EXAMPLE 3

(5S')—N-{[5-(Ethylsulfonyl)pyridine-2-yl]methyl}-5'-methyl-1-{(1R)-1-[2-(trifluoromethyl)pyrimidin-5-yl]ethyl}-4',5'-dihydrospiro[piperidine-4,7'thieno[2,3-C]pyran]-2'-carboxamide

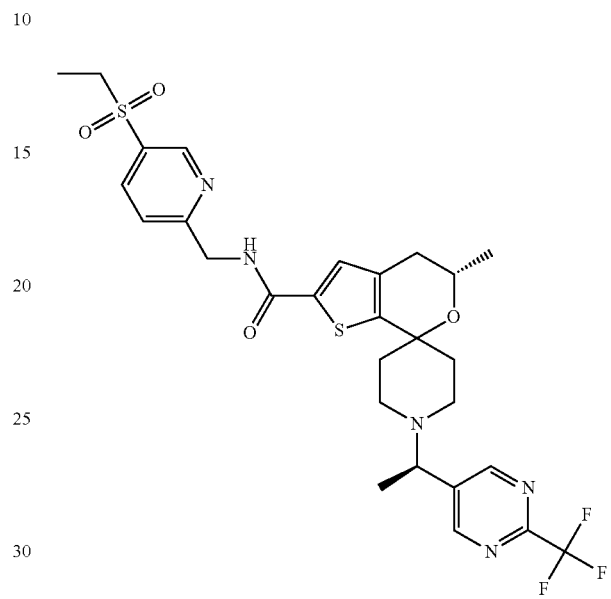

EXAMPLE 4

(5R')—N-{[5-(Ethylsulfonyl)pyridine-2-yl]methyl}-5'-methyl-1-{1-[2-(trifluoromethyl)pyrimidin-5-yl]ethyl}-4',5'-dihydrospiro[piperidine-4,7'thieno[2,3-C]pyran]-2'-carboxamide isomer 1

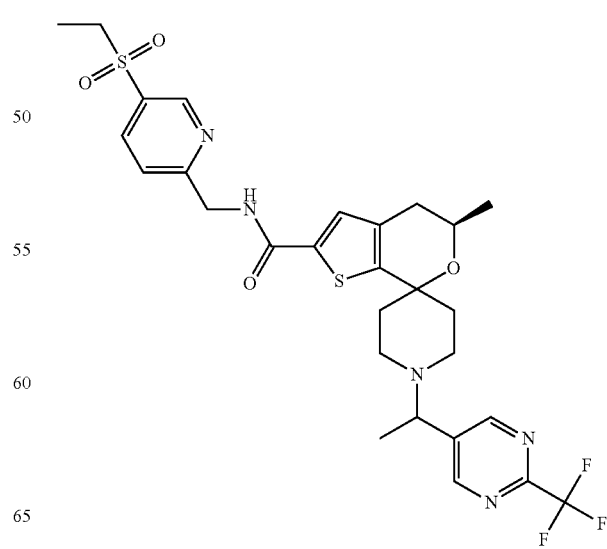

EXAMPLE 5

(5R')—N-{[5-(Ethylsulfonyl)pyridine-2-yl]methyl}-5'-methyl-1-{1-[2-(trifluoromethyl)pyrimidin-5-yl]ethyl}-4',5'-dihydrospiro[piperidine-4,7'thieno[2,3-C]pyran]-2'-carboxamide isomer 2

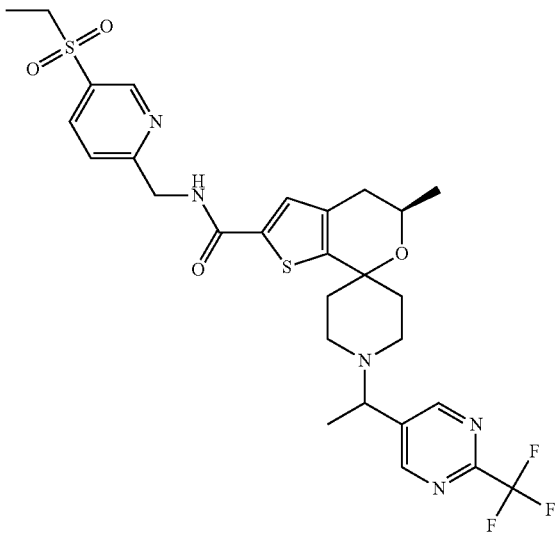 [SMILES: CCS(=O)(=O)c1ccc(CNC(=O)c2cc3c(s2)C2(CCN(C(C)c4cnc(C(F)(F)F)nc4)CC2)O[C@H](C)C3)nc1]

Dissolve N-{[5-(ethylsulfonyl)pyridine-2-yl]methyl}-5'-methyl-1-{1-[2-(trifluoromethyl)pyrimidin-5-yl]ethyl}-4',5'-dihydro spiro[piperidine-4,7'thieno[2,3-C]pyran]-2'-carboxamide (1.28 g, 2.05 mmol) in MeOH (58.5 mL). Separate via chiral chromatography by SFC [AD-IC column (30×250 mm, 5μ) and eluting with 50% IPA (20 mM NH₃) at 120 mL/minute with an injection of 4.5 mL (200 mg) every 10 minutes to give Example 5, (5R')—N-{[5-(ethylsulfonyl)pyridine-2-yl]methyl}-5'-methyl-1-{1-[2-(trifluoromethyl)pyrimidin-5-yl]ethyl}-4',5'-dihydro spiro[piperidine-4,7'thieno[2,3-C]pyran]-2'-carboxamide isomer 2 and mixed fractions containing, Example 2, (5S')—N-{[5-(ethylsulfonyl)pyridine-2-yl]methyl}-5'-methyl-1-{(1S)-1-[2-(trifluoromethyl)pyrimidin-5-yl]ethyl}-4',5'-dihydro spiro[piperidine-4,7'thieno[2,3-C]pyran]-2'-carboxamide, Example 3, (5S')—N-{[5-(ethylsulfonyl)pyridine-2-yl]methyl}-5'-methyl-1-{(1R)-1-[2-(trifluoromethyl)pyrimidin-5-yl]ethyl}-4',5'-dihydrospiro[piperidine-4,7'thieno[2,3-C]pyran]-2'-carboxamide and Example 4, (5R')—N-{[5-(ethylsulfonyl)pyridine-2-yl]methyl}-5'-methyl-1-{1-[2-(trifluoromethyl)pyrimidin-5-yl]ethyl}-4',5'-dihydrospiro[piperidine-4,7'thieno[2,3-C]pyran]-2'-carboxamide isomer 1. Concentrate the mixed fractions and dissolve them in MeOH (55.5 mL). Separate the mixture via chiral chromatography by SFC [OJ-H column (30×250 mm, 5μ) and eluting with 22% MeOH (20 mM NH₃) at 160 mL/minute, injection of 5.0 mL every 5 minutes to give Example 4, (5R')—N-{[5-(ethylsulfonyl)pyridine-2-yl]methyl}-5'-methyl-1-{1-[2-(trifluoromethyl)pyrimidin-5-yl]ethyl}-4',5'-dihydrospiro[piperidine-4,7'thieno[2,3-C]pyran]-2'-carboxamide isomer 1 and a mixture of Example 3, (5S')—N-{[5-(ethylsulfonyl)pyridine-2-yl]methyl}-5'-methyl-1-{(1R)-1-[2-(trifluoromethyl)pyrimidin-5-yl]ethyl}-4',5'-dihydrospiro[piperidine-4,7'thieno[2,3-C]pyran]-2'-carboxamide and Example 2, (5S')—N-{[5-(ethylsulfonyl)pyridine-2-yl]methyl}-5'-methyl-1-{(1S)-1-[2-(trifluoromethyl)pyrimidin-5-yl]ethyl}-4',5'-dihydrospiro[piperidine-4,7'thieno[2,3-C]pyran]-2'-carboxamide Concentrate the mixed fractions and dissolve them in MeOH (30.0 mL). Separate the mixture via chiral chromatography by SFC [AD-H column (50×250 mm, 5μ) and eluting with 50% IPA (20 mM NH₃) at 200 mL/min, injection of 3.0 mL every 32 minutes to give Example 2, (5S')—N-{[5-(ethylsulfonyl)pyridine-2-yl]methyl}-5'-methyl-1-{(1S)-1-[2-(trifluoromethyl)pyrimidin-5-yl]ethyl}-4',5'-dihydrospiro[piperidine-4,7'thieno[2,3-C]pyran]-2'-carboxamide and Example 3, (5S')—N-{[5-(ethylsulfonyl)pyridine-2-yl]methyl}-5'-methyl-1-{(1R)-1-[2-(trifluoromethyl)pyrimidin-5-yl]ethyl}-4',5'-dihydro spiro[piperidine-4,7'thieno[2,3-C]pyran]-2'-carboxamide Concentrate each set of pure fractions, then dissolve the separated products in acetonitrile (0.6 mL), add water, freeze at −78° C., and lyopholyze to give Example 2, 0.214 g, 16%, 99.5% ee, $R_f$=2.94 minutes, mass spectrum (m/z): 624 (M+H). Example 3, 0.203 g, 15%, 98.9% ee, $R_f$=2.75 minutes, mass spectrum (m/z): 624 (M+H). Example 4, 0.251 g, 17%, 98.3% ee, $R_f$=4.75 minutes, mass spectrum (m/z): 624 (M+H). Example 5, 0.272 g, 18%, 100% ee, $R_f$=4.33 minutes, mass spectrum (m/z): 624 (M+H). Analytical conditions: SFC (220 nm UV), column: AD-IC 30×250 mm, 5μ, mobile phase: 50% IPA (20 mM NH₃). Chiral LC analytical conditions: SFC (225 nm UV), column Chirocel OJ-H, 20% MeOH (0.2% isopropylamine)/CO₂, 5 mL/min.

Alternate Preparation of Example 2

(5S')—N-{[5-(Ethylsulfonyl)pyridine-2-yl]methyl}-5'-methyl-1-{(1S)-1-[2-(trifluoromethyl)pyrimidin-5-yl]ethyl}-4',5'-dihydrospiro[piperidine-4,7'thieno[2,3-C]pyran]-2'-carboxamide

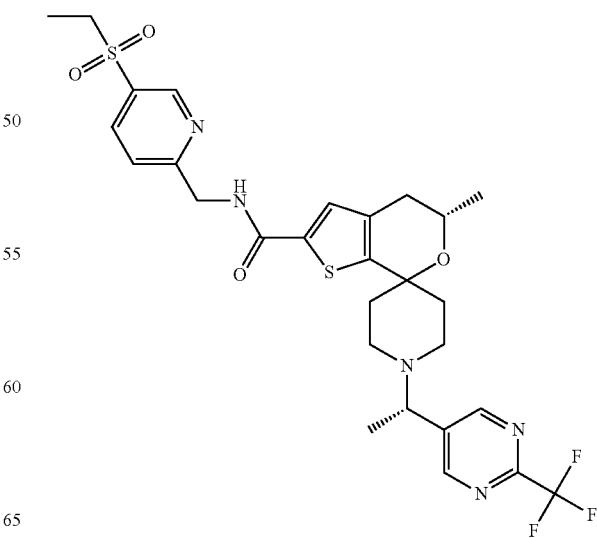

And Alternate Preparation of Example 3

(5S')—N-{[5-(Ethylsulfonyl)pyridine-2-yl]methyl}-5'-methyl-1-{(1R)-1-[2-(trifluoromethyl)pyrimidin-5-yl]ethyl}-4',5'-dihydrospiro[piperidine-4,7'thieno[2,3-C]pyran]-2'-carboxamide

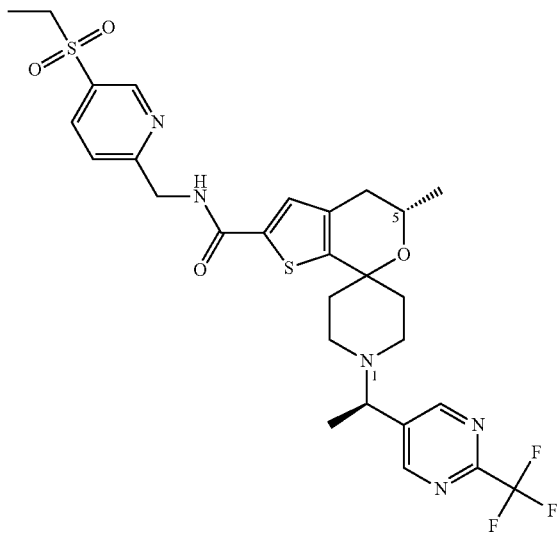 [SMILES: CCS(=O)(=O)c1ccc(CNC(=O)c2cc3c(s2)C2(CCN([C@H](C)c4cnc(C(F)(F)F)nc4)CC2)O[C@@H](C)C3)nc1]

Dissolve (5S')—N-{[5-(ethylsulfonyl)pyridine-2-yl]methyl}-5'-methyl-4',5',dihydrospiro[piperidine-4,7'-thieno[2,3,c]pyran]-2'-carboxamide dihydrochloride (28.28 g, 58.19 mmol) in acetonitrile (280 mL) and diisopropylethylamine (50 mL, 290.9 mmol) and add 5-(1-bromoethyl)-2-(trifluoromethyl) pyrimidine (0.71 g, 2.77 mmol), then stir at ambient temperature overnight. Concentrate under reduced pressure, then dissolve the crude mixture in DCM and purify with silica gel chromatography eluting with 100% EtOAc to give the mixture of title compounds. Separate via chiral chromatography [Chiralpak IA column (8×40.5 cm, 225 nm) and eluting with 40% acetonitrile/60% isopropylalcohol (with 0.2% dimethylethylamine) at 400 mL/minute, injection of 20 mL (2000 mg). Concentrate each diastereomer under reduced pressure, then dissolve in hot ethanol (250 mL), filter hot, then allow to cool to ambient temperature, and rinse with cold ethanol. Dry the solid in a vacuum oven at 55° C. to give Example 2, 9.94 g, 27%, 90.8% ee, $R_t$=3.93 minutes, mass spectrum (m/z): 624 (M+H) and Example 3, 9.42 g, 26%, 98.8% ee, $R_t$=9.25 minutes, mass spectrum (m/z): 624 (M+H)) as crystalline material. Analytical conditions: Chiralpak IA column (4.6×150 mm, 225 nm) and eluting with 40% acetonitrile/60% isopropylalcohol (with 0.2% dimethylethylamine) at 1 mL/minute.

X-Ray Diffraction

Example 3

Mount a single crystal on a thin MiTeGen fiber at 23° C. Collect the data using a CuK$_\alpha$ radiation source ($\lambda$=1.54178 Å) and a Bruker D8 based 3-circle goniometer diffractometer equipped with a SMART 6000CCD area detector (Bruker-AXS. SHELXTL (V2013 6.2) Madison, Wis., USA). Perform cell refinement and data reduction using the SAINT program V8.32b (Sheldrick, G. M., (2008), *SHELXS*-97, *Acta Cryst*. A64, 112-122). Index the unit cell having monoclinic parameters of a=10.1624(2) Å, b=9.9080 (2) Å, c=15.1085(3) Å, and α=90°, β=100.6879(14°), γ=90°. The cell volume of crystal structure is 1494.87(5) Å$_3$. The calculated density of the structure is 1.386 g/cm$^3$ at 23° C. Solve the structure by direct methods (Sheldrick, G. M., (2008), *SHELXS*-97, *Acta Cryst*. A64, 112-122). All atomic parameters were independently refined. The space group choice, that is P2$_1$, is confirmed by successful convergence of the full-matrix least-squares refinement on F$^2$ (Sheldrick, G. M., (2013), *SHELXL*-2013, Program for crystal structure refinement, Institute fur anorg chemie, Göttingen, Germany) with a final goodness of fit of 1.088. The final residual factor, R is =0.0771 and the largest difference peak and hole after the final refinement cycle were 0.315 and −0.333 (e.A$^{-3}$), respectively. The absolute structure parameter refined to 0.072(17).

The structure of Example 3 is determined and the molecular structure is consistent with that shown for Example 3. It should be noted that the crystal structure is of high quality and establishes the absolute stereochemistry of the chiral centers of Example 3 C5 as (S) and C1 as (R) off the piperdine group by using the anomalous scattering contribution of the heavy atom (sulfur) in the structure. The absolute configuration is determined from the crystal structure to be (5'S)—N-{[5-(ethylsulfonyl)pyridin-2-yl]methyl}-5'-methyl-1-{(1R)-1-[2-(trifluoromethyl)pyrimidin-5-yl]ethyl}-4',5'-dihydrospiro[piperidine-4,7'-thieno[2,3-c]pyran]-2'-carboxamide configuration.

Biological Assays

RORa, b, and g Binding Inhibitors

His-tagged human RAR-related orphan receptor alpha (hRORa), human RAR-related orphan receptor beta (hRORb), and human RAR-related orphan receptor gamma (hRORg) are used for receptor-ligand competition binding assays to determine $K_i$, values. Typical procedures are provided below.

Receptor competition binding assays are run in a buffer made up of DPBS (1 L) (Hyclone #SH30028.03), 2.2 g BSA Fraction v (Roche #9048-46-8), 100 mL glycerol (Fischer #56-81-5) and 40 mL DMSO (reagent grade). The final wells contain 20 μg/mL aprotinin and 20 μg/mL leupeptin and 10 μM Pefabloc. Typically, receptor binding assays include radio-labeled ligands, such as 7 nM [$^3$H]-25-hydroxycholesterol for alpha binding, 20 nM [$^3$H]-3-[[4-[[3-(2,6-dichlorophenyl)-5-isopropyl-isoxazol-4-yl]methoxy]-N,2-dimethyl-anilino]methyl]benzoic acid for beta binding, and 6 nM [$^3$H]-25-hydroxycholesterol for gamma binding, and 0.5 μg RORa receptor, 0.03 μg RORb receptor, or 0.13 μg RORg receptor per well. Assays are typically run in 96-well format. Competing test compounds are added at various concentrations ranging from about 0.4 nM to 25 μM. Non-specific binding is determined in the presence of 250 nM 25-hydroxycholesterol for RORa and RORg binding, 250 nM 3-[[4-[[3-(2,6-dichlorophenyl)-5-isopropyl-isoxazol-4-yl]methoxy]-N,2-dimethyl-anilino]methyl]benzoic acid for RORb binding. The sample, label and receptor solutions are combined in a 96 well assay plate (Costar 3632) and incubated overnight at room temperature, then 25 μl beads (Amersham YSi (2-5 micron) copper His-tag Spa Beads, #RPNQ0096) for a final bead concentration of 1 mg/well is added to each reaction. Plates are mixed for 30 minutes on an orbital shaker at room temperature. After an incubation of 4 hours, plates are read in a Wallac MICROBETA® counter.

The data are used to calculate an estimated $IC_{50}$ using a four parameter logistic fit. The Kd for [$^3$H]-25-hydroxycholesterol for RORa and RORg, and [$^3$H]-3-[[4-[[3-(2,6-dichlorophenyl)-5-isopropyl-isoxazol-4-yl]methoxy]-N,2-dimethyl-anilino]methyl]benzoic acid for RORb binding, is determined by saturation binding. The $IC_{50}$ values for compounds are converted to Ki using the Cheng-Prushoff equation.

The results of the following exemplified compounds are shown in Table 2 below.

TABLE 2

| Example # | RORa Ki (nM) | RORb Ki (nM) | RORg Ki (nM) |
|---|---|---|---|
| 1 | >20,400 | >12500 | 12.0 ± 7.3, n = 2 |
| 2 | >20,400 | >12500 | 6.24 ± 0.73, n = 2 |
| 3 | >20,400 | >12500 | 16.6 ± 8.8, n = 5 |
| 4 | >20,400 | 2190 | 148 ± 40, n = 2 |
| 5 | >20,400 | 407 | 153 ± 25, n = 2 |

Mean + SEM; SEM = standard error of the mean

These results demonstrate that the compounds of Table 2 are selective for RORg versus RORa and RORb.

HEK293 RORg GAL4 Receptor-Reporter Assay

As an indicator of inverse agonist activity, an RAR-related orphan receptor gamma (RORg) receptor-reporter assay (RORg-GAL4/pGL4.31) is performed in HEK293 cells. HEK293 cells are co-transfected using Fugene™ reagent. A reporter plasmid containing a GAL4 binding domain and a minimal adenoviral promoter upstream of a firefly luciferase gene is co-transfected with a plasmid constitutively expressing a human RORg ligand binding domain fused to yeast GAL4 DNA binding domain. Cells are transfected in T150 cm$^2$ flasks in MEM media without FBS. After 18 hours incubation, transfected cells are trypsinized, plated in 96-well microtiter plates in 3:1 DMEM-F12 media containing 10% FBS, incubated for 4 hours and then exposed to various concentrations of test compounds ranging from about 0.05 nM to 10 µM. After 18 hours of incubations with compounds, cells are lysed and luciferase activity is quantified using standard techniques. Data is fit to a 4 parameter-fit logistics to determine $IC_{50}$ values.

The results of the following exemplified compounds are shown in Table 3 below.

TABLE 3

| Example # | $hIC_{50}$(nM) |
|---|---|
| 1 | 56.5 ± 39.4, n = 2 |
| 2 | 45.8 ± 8.5, n = 4 |
| 3 | 21.8 ± 7.03, n = 7 |
| 4 | 97.9 ± 5.1, n = 2 |
| 5 | 59.5 ± 1.3, n = 2 |

Mean + SEM; SEM = standard error of the mean

These results demonstrate that the compounds of Table 3 are inverse agonists for human RORg receptor.

PBMC IL-17 Secretion ELISA and Cell TiterGlo Viabiltiy Assay

PBMC's are isolated from whole blood buffy coats by first combining fresh buffy coats with equal volumes of phosphate buffered saline. Thirty five mL of PBS/buffy coat solution are then gently overlaid onto 15 mL of Ficoll in 50 mL conical tubes. Following centrifugation for 30 minutes at 500×g (with slow acceleration and deceleration) the top layer of plasma is discarded and the layer of cells along the Ficoll interface is collected and pooled. Each 250 mL tube is filled to the top with room temperature RPMI-1640 media. Tubes are spun for 10 minutes at 500×G (with slow acceleration and deceleration), the media is removed by aspiration, and the wash step is repeated. Cells are resuspended in ice cold Recovery Cell Culture Freezing Medium from Life Technologies (Catalog number 12648-010) on ice. The cell concentration is adjusted to 66.7 million cells/mL. Cell are slow frozen at −1° C./minute in vials with 100 million cells and stored in liquid nitrogen.

Stimulation of IL-17 Secretion and Compound Addition

PBMC are brought out of thaw by resuspending with 1 mL of complete media (RPMI-1640 containing 30 mM HEPES, 100 units/mL penicillin, 100 µg/mL streptomycin, 3.25 mM L-Glutamine, 0.2 µM beta-mercaptoethanol, and 10% FBS) followed by the drop wise addition of 2 mL, 4 mL, 8 mL, and 16 mL of complete media with gentle swirling. Cells are spun down for 5 minutes and the cell pellet is resuspended in complete media. Clumps of cells are broken up by running the cell solution through a 23 gauge syringe needle and a 40 µM cell strainer. One hundred thousand cells per well are added to 384 well polystyrene tissue culture treated flat bottomed plates in a total of 30 µL. Stimulation cocktail containing anti-human CD3 antibody, anti-human CD28 antibody, IL-23 and compounds prepared in complete media are added to the cells simultaneously in a total volume of 30 µL. The final concentration of added stimulants is 160 ng/mL, 500 ng/mL, and 5 ng/mL for anti-CD3 antibody, anti-CD28 antibody, and IL-23 respectively and 0.3% for DMSO. Plates are sealed with AERASEAL® sealing film and incubated for 48 hours at 37° C., 95% humidity, and 5% $CO_2$.

Following the incubation period the plates are spun at 200×g for five minutes. Supernatants are diluted 1:1 with equal volume 1% BSA/PBS and tested for IL-17 with a human IL-17 ELISA kit from R&D system (catalog #D317E) according to the protocol provided with the kit with one exception—the colorimetric substrate OPD (o-phenylenediamine dihydrochloride, Sigma Cat #P6912) is used instead of the substrate supplied in the kit. Absorbance at 492 nm is measured with the Envision multi-label plate reader. A492 values are converted to concentration of IL-17 based on the IL-17 standard curve as shown below:
pg/mL IL-17=EC50*[[(Top−Bottom)/(A492−Bottom)]−1] (1/−Hill). $IC_{50}$'s for inhibition of IL-17 secretion is calculated based on converted values using a standard 4-parameter fit with maximum inhibition determined from the average values of wells with no added stimulants nor compounds and minimum inhibition from the average values of wells with stimulants alone and no added compound.

Equal volumes of Cell TITERGLO® cell viability testing reagent (Promega Cat# G7573) are added to the cells remaining in the plates, and following a fifteen minute incubation with gentle shaking at room temperature luminescence is measured with the Envision multi-label plate reader. Percent cell death is calculated by setting 100% activity (cell death) to zero luminescence units and minimum activity (max number of viable cells) as the average luminescence units of wells containing stimulants alone and no added compound. $IC_{50}$'s are calculated using a standard four parameter fit.

The results of the following exemplified compounds are shown in Table 4 below.

TABLE 4

| Example # | hPBMC IL-17 ELISA (nM) | Cell TiterGlo Viability ($EC_{50}$) |
|---|---|---|
| 1 | 77.3 | >1.0 µM |
| 2 | 33.7 ± 33.1, n = 6 | >1.0 µM |
| 3 | 20.0 ± 12.6, n = 12 | >1.0 µM |
| 4 | 106 | >1.0 µM |
| 5 | 30.5 ± 29.3, n = 4 | >1.0 µM |

Mean + SEM; SEM = standard error of the mean

These results show that the compounds of Table 4 inhibit anti-CD3/anti-CD28/IL-23 stimulated IL-17 secretion in PBMC's without measurable cytotoxic effect.

Glucose-6-Phosphate Isomerase (GPI) Induced Arthritis Model

The GPI induced arthritis model is adapted from K. Iwanami et al *Arthritis Rheumatism* 58, 754-763, 2008 and D. Schubert et al. *J Immunology* 172, 4503-4509, 2004. Mice (8-9 week old male DBA/1 mice) (Harlan) are randomly assigned into treatment groups based on body weights collected on the day of immunization (day 0). On the day of immunization (day 0), a 1:1 (v:v) mixture of recombinant human GPI (diluted to 4 mg/mL in PBS, Gibco) and complete Freund's adjuvant (CFA, Sigma) is mixed on a high speed homogenizer (Omni) for 40 minutes in a cold room. A final concentration of 2 mg/mL GPI is achieved in the emulsion. Mice are injected at the base of the tail (2 sites of injection, subcutaneously, 100 µL each site) with the GPI emulsion. Test compounds are dosed orally starting on the same day as immunization (day 0). Starting on day 0, each paw is scored for severity of joint swelling based on a 0 to 3 scoring system (See K. Iwanami et al *Arthritis Rheumatism* 58, 754-763, 2008. The clinical score represents the total score of all 4 paws (maximum score=12). Clinical scores are assessed on days 0, 2, 4, 7, 8, 9, 10, 11, 12, 14, 16, 18, and 21.

The AUC is calculated by a trapezoid method for clinical score over time from the day of immunization (day 0) to day 21. Test p-values were derived from Student's t-test.

Example 3 (1000 mg/Kg) and vehicle (1% HEC, 0.25% Polysorbate 80, and 0.05% Antifoam in purified water) treatments (n=8/group) are initiated on day 0 and administered orally once daily. Example 3 reduces severity of paw swelling and maintains lower mean clinical scores through the course of disease compared to the vehicle group. This effect results in 75% reduction in clinical score AUC, a cumulative measure of paw swelling over time, that is statistically significant compared to the vehicle group as shown in Table 5.

TABLE 5

| Treatment | Clinical Score AUC (mean ± SEM) |
|---|---|
| Vehicle | 87.70 ± 4.88 |
| Example 3 | 22.20 ± 8.68* |

Values are shown as mean ± SEM.
*p < 0.05 vs. Vehicle (Student's t-test).
SEM = standard error of the mean

I claim:

1. A compound of formula

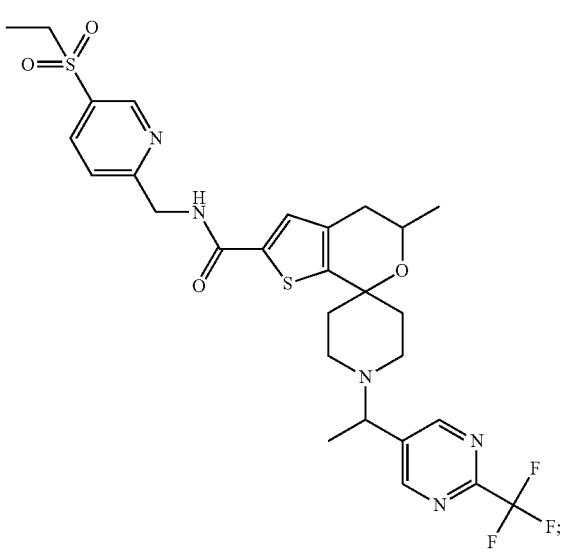 [SMILES: CCS(=O)(=O)c1ccc(CNC(=O)c2cc3c(s2)C2(CCN(C(C)c4cnc(C(F)(F)F)nc4)CC2)OC(C)C3)nc1]

or a pharmaceutically acceptable salt thereof.

2. The compound of claim 1 of formula

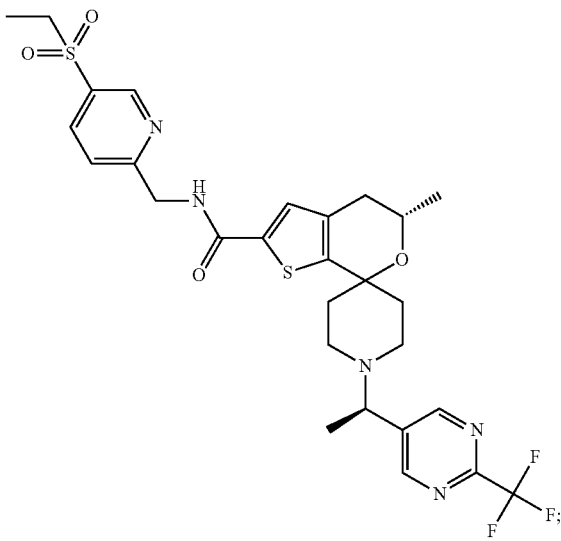 [SMILES: CCS(=O)(=O)c1ccc(CNC(=O)c2cc3c(s2)C2(CCN([C@H](C)c4cnc(C(F)(F)F)nc4)CC2)O[C@@H](C)C3)nc1]

or a pharmaceutically acceptable salt thereof.

3. The compound of claim 1 of formula

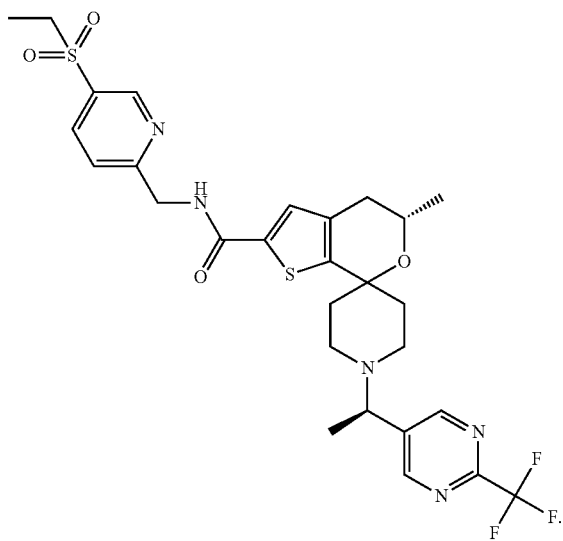 [SMILES: CCS(=O)(=O)c1ccc(CNC(=O)c2cc3c(s2)C2(CCN([C@H](C)c4cnc(C(F)(F)F)nc4)CC2)O[C@@H](C)C3)nc1]

4. A pharmaceutical composition comprising a compound of claim 1, or a pharmaceutically acceptable salt thereof, in combination with one or more pharmaceutically acceptable carriers, diluents, or excipients.

5. The pharmaceutical composition according to claim 4 comprising one or more other therapeutic agents.

6. A method of treating psoriasis comprising administering a compound of claim 1, or a pharmaceutically acceptable salt thereof, to a patient in need thereof.

7. A method of treating seronegative spondylarthropathies comprising administering a compound of claim 1, or a pharmaceutically acceptable salt thereof, to a patient in need thereof.

8. The method according to claim 7 for treating axial spondyloarthritis, ankylosing spondylitis, or psoriatic arthritis.

* * * * *